United States Patent [19]

Cidaria et al.

[11] Patent Number: 5,120,536
[45] Date of Patent: Jun. 9, 1992

[54] BACILLUS THURINGIENSIS VAR. DONEGANI PREPARATE OR TOXIN OBTAINED FROM IT, ENDOWED WITH INSECTICIDE ACTIVITY AGAINST COLEOPTERA

[75] Inventors: Dante Cidaria, Novara; Andrea Cappai, Venice; Adriana Vallesi, Novara; Vincenzo Caprioli, S. Martino Siccomario; Giorgio Pirali, Saronno, all of Italy

[73] Assignee: Presidenza del Consiglio dei Ministri-Ufficio del Ministro per il Coordinamento delle Iniziative per la Ricerca Scientificia e Tecnologica, Rome, Italy

[21] Appl. No.: 560,848

[22] Filed: Jul. 31, 1990

[30] Foreign Application Priority Data

Aug. 1, 1989 [IT] Italy .................. 21412 A/89

[51] Int. Cl.$^5$ .................. C12N 1/20; A61K 39/07; A01N 63/00; A01N 25/12
[52] U.S. Cl. .................. 424/93 L; 435/252.1; 435/252.5; 435/832; 435/252.3; 530/350

[58] Field of Search ............ 424/93; 405/252.1, 252.5, 405/832, 252.3; 530/350

[56] References Cited

U.S. PATENT DOCUMENTS

| | | | |
|---|---|---|---|
| 4,766,203 | 8/1988 | Krieg et al. | 424/93 X |
| 4,771,131 | 9/1988 | Herrnstadt et al. | 424/93 |
| 4,849,217 | 7/1989 | Soares et al. | 424/93 |
| 4,865,981 | 9/1989 | Herrnstadt et al. | 435/252.3 |
| 4,910,016 | 3/1990 | Gaertner et al. | 424/93 |
| 4,948,734 | 8/1990 | Edwards et al. | 424/93 X |
| 4,950,471 | 8/1990 | Travers et al. | 424/93 |
| 4,966,765 | 10/1990 | Payne et al. | 424/93 |

FOREIGN PATENT DOCUMENTS 202739 11/1986 European Pat. Off. .

Primary Examiner—Howard E. Schain
Assistant Examiner—P. Lynn Touzeau
Attorney, Agent, or Firm—Morgan & Finnegan

[57] ABSTRACT

Disclosed is a *Bacillus thuringiensis* var. donegani, pathotype C, NCIMB 40152 and a preparate or a toxin obtained from it, endowed with insecticide activity against Coleoptera.

5 Claims, No Drawings

BACILLUS THURINGIENSIS VAR. DONEGANI PREPARATE OR TOXIN OBTAINED FROM IT, ENDOWED WITH INSECTICIDE ACTIVITY AGAINST COLEOPTERA

FIELD OF THE INVENTION

The present invention relates to a variety of *Bacillus thuringiensis*, denominated "var. donegani" (Btd) NCIMB 40152, to a preparate or a toxin obtained from it, endowed with insecticide activity against Coleoptera.

BACKGROUND OF THE INVENTION

It is known that the sporogenous bacillus *Bacillus thuringiensis* (Bt) produces, during the sporogenesis step, parasporal crystals of proteinic nature and displaying an insecticide activity against a large number of insects belonging to the orders of Lepidoptera, Diptera and Coleoptera. Such crystals, when ingested by an insect sensitive to their activity, cause irreversible damages to its intestinal mucosa, with the insect consequently stopping feeding and undergoing death.

Many varieties of Bt are known, which differ from one another on the basis of biochemical and/or physiological parameters, and of their specific/selective insecticide activity. Some of these varieties are traded as formulates for use in the fight against insects.

The Bt varieties known heretofore are subdivided on the basis of their specific/selective activity, into three pathotypes:

| Pathotype | Specific insecticide activity | Main varieties |
|---|---|---|
| A | Lepidoptera | kurstaki |
| B | Diptera | israelensis |
| C | Coleoptera | tenebrionis san diego |

As pathotype C, endowed with specific activity against coleopters, only two varieties are known in the art, i.e., var. 1 tenebrionis, claimed in European patent application No. EPO 149,162 and var. san dieco, claimed in EPO 202,739.

DETAILED DESCRIPTION OF THE INVENTION

The purpose of the invention is to provide a Bt variety, an insecticide preparate or a toxin obtained from it, endowed with a superior specific insecticide activity against coleopters, the preparation of which is simpler, cheaper and more effective.

A variety of *Bacillus thuringiensis*, pathotype C, denominated var. doneqani (Btd) NCIMB 40152 and the relevant insecticide preparate or toxin has been found now which, besides resulting in more advantages compared to the Bt's, pathotype C, known heretofore, thanks to its insecticide activity of covering type, preparation and application in the agrarian field, results unexpectedly with a systemic insecticide activity.

Therefore, the subject matter of the present invention is *Bacillus thuringiensis* variety donegani NCIMB 40152 or a biologically pure culture thereof.

Another subject matter of the instant invention is the crystalline, parasporal proteinic toxin obtained from cultures of *Bacillus thuringiensis* variety doneqani NCIMB 40152 after the sporogenesis and the successive lysis of sporangium.

A further subject matter of the instant invention is an insecticide preparation containing as its active principle the crystalline, parasporal proteinic toxin obtained from cultures of *Bacillus thuringiensis* variety doneqani NCIMB 40152 after the sporogenesis and the successive lysis of sporangium.

Still another subject matter of the present invention is an insecticide preparate, wherein the active principle is constituted by the solid lyophilized products obtained from the fermentation and sporogenesis of Btd NCIMB 40152.

Still a further subject matter of the instant invention is a method for fighting insects, in particular coleopters, which method consists in spreading the plants or their parts, such as stems, leaves, or the ground on which they are grown, with a suitable amount of Btd NCIMB 40152, a preparate or a toxin derived from it, as such or as a suitable composition, comprising inert, solid or liquid, vehicles and other additives.

*Bacillus thurinciensis* var. donegani (Btd) NCIMB 40152 is endowed with a specific insecticide activity against Coleoptera and, in particular, against important agronomical targets, such as leaf beetle *Leptinotarsa decemlineata* (Doriphora of potato), therefore belongs to "pathotype C" according to as described by A. Krieg et al., Z. Ang. Ent. 96 (1983) 500–508.

Btd NCIMB 40152 differs from the known varieties of Bt in that it shows different biochemical and physiological characteristics and, in particular, is different from tenebrionis and san diego varieties also in that it produces a parasporal crystal with different morphological characteristics, as well as with a different behavior from the physical-chemical and physiological viewpoint.

Morphology and Biochemical Characteristics of Btd NCIMB 40152

*Bacillus thuringiensis* var. donegani (Btd) NCIMB 40152 was isolated from larvae of *Tenebrio molitor* dead owing to natural causes, and was catalogued for internal laboratory use with the conventional code BT/43.

The isolation took place on Nutrient Agar medium, rendered selective by the addition of 10 U/ml of Penicillin G. The contents of the insects were preliminary treated at 80° C. for a time of 15–20 minutes, for the purpose of selectively isolating the sporogenous bacilli. A culture of this microorganism was filed on May 31, 1989, in compliance with the Treaty of Budapest with the National Collection of Industrial Bacteria (c/o The National Collection of Industrial and Marine Bacteria Ltd., Torry Research Station, P.O. Box 31, 135 Abbey Road, Aberdeen AB 98 DG, Scotland, U.K.), where it was assigned the access number NCIMB 40152.

Btd NCIMB 40152 can be maintained on common media, e.g., on Nutrient Agar medium at 25°–30° C., and can be propagated by techniques per se known to those skilled in the art.

The determination of the genus and of the species was carried out on the basis of the morphological and biochemical characteristics of the microorganism.

Morphology

The isolated colonies of Btd NCIMB 40152 on Nutrient Agar medium are flat, with an either circular or irregular shape, and an eroded or lobate edge; they are of whitish color. The vegetative cell has the shape of a small rod, is Gram-positive, has a diameter of from 1 to 2 μm, and a length of from 6 to 8 μm.

The growth temperature is comprised within the range of from 25° to 35° C.

When the culture of the microorganism is treated in an autoclave at 121° C. for 15 minutes, both the spores and the toxin are inactivated.

The position of the spore is central, or sub-terminal. The parasporal crystal, observed under the electron scanning microscope, has the shape of a square-base parallelepipedon with two pyramids with equal bases on the upper face and on the lower face, with dimensions comprised within the range of from 1 to 2 μm and therefore is different from the parasporal crystal produced by Bt tenebrionis and san dieco varieties, which is flat and rhomboidal in both cases.

Biochemical Characteristics

Btd NCIMB 40152, in its vegetative step, has the biochemical characteristics reported in Table 1.

TABLE 1

| Test | Response |
| --- | --- |
| Acidification of glucose | + |
| Acidification of mannitol | − |
| Acidification of mannose | − |
| Acidification of saccharose | + |
| Acidification of lactose | − |
| Acidification of arabinose | − |
| Acidification of xylose | − |
| Acidification of salicin | + |
| Hydrolysis of esculin | + |
| Hydrolysis of starch | + |
| Hydrolysis of gelatin | + |
| Production of gas from glucose | − |
| Arginine di-hydrolase | − |
| Lysine decarboxylase | − |
| Phenyl-alanine deaminase | − |
| Urease | − |
| Catalase | + |
| (Soy) lecithinase | + |
| Nitrate reductase | + |
| Voges-Proskauer reaction | + |
| Growth on chitin | − |
| Growth in NaCl at 7% | − |
| Growth at 50° C. | − |
| Growth in 10 U/ml of Penicillin G | + |
| Growth in 10 μg/ml of chloramphenicol | − |
| Growth in 25 μg/ml of streptomycin | − |
| Growth in 30 μg/ml of nalidixic acid | − |
| Growth in 50 μg/ml of lysozime | + |

(As regards the test method used, see: "The Prokaryotes", Springer-Verlag, 1981; "Manual of Methods for General Bacteriology", The American Society for Microbiology, 1981.)

The diversity between Btd 40152 and the varieties known from the prior art can be inferred also by comparing the biochemical characteristics of Btd 40152 to those of the known varieties of Bt, as reported in the following Table 2.

TABLE 2

[After: A. Krieg in "The Prokaryotes", Springer-Verlag, 1981, page 1750; A. Krieg, J. Appl. Ent. 104 (1987), 417-424]

| Variety | MAN | SAC | SAL | AMI | CHT | URE | ARG | LCT |
| --- | --- | --- | --- | --- | --- | --- | --- | --- |
| thuringiensis | + | + | + | + | V | − | + | |
| finitimus | − | + | + | − | + | − | − | |
| alesti | − | − | − | + | V | − | + | |
| kurstaki | − | − | + | + | V | + | + | |
| sotto | − | + | − | + | V | − | − | |
| dendrolimus | − | − | − | + | + | − | V | |
| keniae | − | − | + | + | V | + | + | |
| galleriae | − | − | + | + | V | + | + | |
| canadensis | − | + | + | + | + | − | + | |
| entomocidus | + | + | − | + | − | − | − | |
| aizawai | − | − | + | + | + | + | + | |
| morrisoni | − | + | − | + | V | − | − | |
| tolworti | − | + | + | + | V | − | + | |
| darmstadiensis | − | − | − | + | − | − | + | |
| toumanoffi | − | − | − | + | − | + | + | |
| thompsoni | − | + | + | + | V | + | + | |
| pakistani | − | + | (+) | + | (+) | − | + | |
| israelensis | + | − | − | + | − | − | − | |
| wuhanensis | − | − | + | + | − | | | |
| tenebrionis | + | + | − | + | − | − | + | − |
| san diego | + | + | − | + | − | − | + | − |
| NCIMB 40152 | − | + | + | + | − | − | − | + |

Footnotes to Table 2:
MAN, SAC, SAL, acidification of mannose, saccharose and salicin;
AMI, hydrolysis of starch;
CHT, growth on chitin;
URE, urease;
ARG, arginine dihydrolase;
LCT, lecithinase;
+ = positive response;
− = negative response;
(+) = partially positive response;
V = variable response.

Characteristics Relating to Culture and Methods of Separation of the Active Principle

*Bacillus thuringiensis* var. donegani (Btd) NCIMB 40152 can be cultivated on common liquid media, such as, e.g., Nutrient broth, at 25°-30° C., by techniques known in the art.

At the end of the fermentation and sporogenesis process, the biomass can be separated by centrifuging the fermentation broth.

The so separated biomass can be subsequently submitted to evaporation or lyophilization, to obtain a solid product in powder form endowed with insecticide activity.

The insecticide activity of Btd NCIMB 40152 is substantially due to a parasporal, crystalline toxin of proteinic nature, which is soluble in water at a neutral pH value, differently from the toxin produced by Bt var. tenebrionis and var. san dieco. Therefore, such a toxin can be separated by suspending again in water, at a neutral pH value, the biomass separated by centrifugation from the fermentation broth after the sporogenesis and maintaining the so obtained suspension, with stirring, at room temperature, for a time comprised within the range of from 1 to 12 hours.

After the successive centrifugation or filtration of the aqueous suspension, an aqueous solution, free from spores and fermentation residues, can be recovered, which substantially contains the proteinic toxin, which can be recovered from its solution by known techniques, such as, e.g., lyophilization.

The determination of the molecular weight of the toxin in SDS-electrophoresis on polyacrylamide gel, according to the method by Laemmle (Nature, 227, 680, 1970) evidences two main groups of bands:

* A first group of three bands, with a molecular weight comprised within the range of from 64,000 to 72,000;
* A second group of two bands, with a molecular weight comprised within the range of 34,000 to 36,000.

Biological Activity

Btd NCIMB 40152, the preparate or the toxin obtained from it, shows an insecticide activity, of covering type as well as of systemic type, against Coleoptera, such as, e.g., *Leptinotarsa decemlineata.*

On the contrary, no toxic effects were observed as regards some Lepidoptera such as, e.g., *Spodoptera littoralis* and *Ephestia kuehniella,* as well as on the dipteran *Aedes aegypti.*

The modality of action of the active principle on the larvae of Coleoptera is the same as observed in the past in case of preparates on the basis of Bt "pathotype A": a few hours after the treatment, the larvae stop feeding and die after a time of from 24 to 48 hours. Death takes place owing to the effect of the toxin on the intestinal epithelium of the insect, which undergoes irreversible lesions.

Btd NCIMB 40152, the lyophilized solid products obtained from its fermentation and sporogenesis, as well as its parasporal proteinic toxin as such, or as a suitable composition, is hence useful in the fight against the Coleoptera which infest the agrarian cultivations.

For this purpose, the use of the separated toxin is preferred.

Compared to the toxins obtained from the known varieties of Bt and, in particular, of "pathotype C" varieties tenebrionis and san diego, the toxin derived form Btd NCIMB 40152 according to the present invention, shows a large number of advantages at the financial-industrial level, relevant to its recovery, to its application and to its insecticide activity.

Such advantages are, e.g.:

* The separation of the toxin from the culture medium is simpler and easier, thanks to the solubility of the same toxin in water and, as a consequence, said toxin can be obtained in concentrated form free from spores, cells and fermentation residues.
* The concentrated aqueous solutions of the toxin-which, differently from the suspensions or dispersions of the toxins known from the prior art, does not settle—can be stored and transported more easily.
* The toxin can be applied from its solutions more easily and effectively than the analogous toxins, which are applied dispersed in the solid form, owing to their incompatibility with the customary organic solvents used in formulations.

Furthermore, the present Applicant has surprisingly and advantageously found that the toxin derived from Btd NCIMB 40152, besides being endowed with an insecticide activity of covering type, shows also a systemic insecticide activity, differently from the toxins produced by other varieties of Bt.

Such a systemic activity, which essentially consists in that the active principle migrates to plant parts even very far away from the application point, ensures a wider protection of the plant and makes possible smaller amounts of active principle to be used: in particular, the toxin according to the present invention moves via the root apparatus of the plants.

Furthermore, the toxin can be effective for longer time periods in that, by penetrating the vascular system of the plant, it is more protected from the external agents, which would tend to cleave it or to wash it away.

The systemic activity of the toxin is even more advantageous when the treatment relates to plants which are in their growth step, and which hence offers to the insect young sprouts, grown later than the treatment date.

Furthermore, the systemic activity endows the toxin with a higher efficacy in preventive treatments; and decreases the need for the treatments to be repeated during the plant growth cycle.

*Bacillus thuringiensis* var. donegani (Btd) NCIMB 40152, the product obtained from its fermentation and sporogenesis, as well as its parasporal toxin, can be formulated as concentrated liquids, wettable powders, by using liquid or solid inert vehicles, and formulation auxiliaries and/or additives, such as wetting agents, adhesion promoters, surfactants, U.V. stabilizers and still other additives as normally used in insecticide formulations.

For the practical uses in agriculture, doses are suitable which, as referred to the toxin derived from Btd NCIMB 40152, are comprised within the range of from 0.05 to 4 kg/hectare, and are preferably comprised within the range of from 0.2 to 2 kg/hectare.

EXAMPLES

Some Examples are reported as follows to illustrate the present invention.

EXAMPLE 1

Erlenmeyer flasks of 500 ml of capacity, containing 100 ml of a medium consisting of Tryptone Soy Broth (OXOID) are inoculated with 1 ml of a 16-hours-old culture of *Bacillus thuringiensis* NCIMB 40152 in Nutrient Broth as the medium.

The Erlenmeyer flasks are kept with orbital stirring at temperature comprised within the range of from 25° to 35° C. The sporogenesis is checked on the microscope. At fermentation end, the biomass is centrifuged off, is suspended again in water at pH 7 and is kept with stirring for 3 hours at room temperature. The solution obtained after separation by centrifuging off the spores and the fermentation residues, is lyophilized and is used for the determinations of biological activity, or for the preparation of the formulates.

EXAMPLE 2

Determinations of insecticide activity of the lyophilized preparate obtained according to Example 1, substantially constituted by the parasporal proteinic toxin, were carried out by using said preparate as an aqueous solution at various concentrations.

The modalities of execution of the activity tests, according to the insect used, are detailed in the following:

LEPTINOTARSA DECEMLINEATA

Covering activity

Second-age larvae are fed with young potato plants treated by dipping with the aqueous solution of the lyophilized toxin as disclosed in Example 1.

The environmental conditions during the observation time are:
* temperature: 25° C.±1° C.
* relative humidity: 60%±2%

The end determination of death rate is carried out 48 hours after the infection; the results are reported in Table 3.

Systemic activity

Second-age larvae of the insect are fed with young potato plants respectively maintained for 12 hours and 24 hours in a hydroponic culture containing the lyophilized product prepared in Example 1, dissolved at the concentration of 200 ppm.

After maintaining the larvae for 48 hours in a conditioned environment, at 25° C. and with a R.H. of 60%, a death rate of 100% was determined in both tests.

TRIBOLIUM CONFUSUM, TENEBRIO MOLITOR, EPHESTIA KUHENIELLA

Third-age larvae are grown under controlled conditions, at a temperature of 25° C.±1° C., with a relative humidity of 65%±2%, in white meal to which the lyophilized product of Example 1 is previously added.

The death rate is determined after 14 days of the infestation; the results are reported in Table 3.

AEDES AEGYPTI

Activity

Third-age larvae are transferred in distilled water containing the lyophilized preparate of Example 1. The larvae are maintained under controlled conditions at 25° C.±1° C., with a relative humidity of 60%, and are fed daily. The death rate, reported in Table 3, is measured after 5 days of treatment.

SPODOPTERA LITTORALIS

Covering activity

Second-age larvae are fed with tobacco leaves treated by dipping with the aqueous solution of the lyophilized product as disclosed in Example 1.

The environmental conditions during the observation period are:
*temperature 25° C.±1° C.
*relative humidity 60%±2%

The determination of death rate is carried out 5 days after the infection; the results are reported in Table 3.

TABLE 3

| Order | Species | Dosis (ppm) | Death rate |
|---|---|---|---|
| Coleoptera | Leptinotarsa decemlineata | 100 | 100% |
| | Tenebrio molitor | 1.000 | 100% |
| | Tribolium confusum | 1.000 | 100% |
| Lepidoptera | Ephestia kuehniella | 1.000 | 0% |
| | Spodoptera littoralis | 500 | 0% |
| Diptera | Aedes aegypti | 500 | 0% |

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

What we claim is:

1. *Bacillus thuringiensis* variety donegani NCIMB 40152 or a biologically pure culture thereof.

2. Crystalline, parasporal proteinic toxin obtained from cultures of *Bacillus thurinciensis* variety donegani NCIMB 40152 after the sporogenesis and the successive lysis of sporangium.

3. An insecticide preparation containing as its active principle the crystalline, parasporal proteinic toxin obtained from cultures of *Bacillus thuringiensis* variety donegani NCIMB 40152 after the sporogenesis and the successive lysis of sporangium.

4. An insecticide preparation, wherein the active principle is constituted by the solid products, lyophilized, obtained from the fermentation and sporogenesis of *Bacillus thuringiensis* variety donegani NCIMB 40152.

5. Method for fighting insects belonging to the order of Coleoptera, comprising spreading plants or their parts, including stems, leaves, or the ground on which they are grown, with an effective amount of *Bacillus thuringiensis* variety donegani NCIMB 40152, a preparate or a toxin derived from it, alone or in composition, comprising inert, solid or liquid vehicles and additives.

* * * * *